United States Patent
Rivers et al.

(10) Patent No.: US 7,063,990 B2
(45) Date of Patent: Jun. 20, 2006

(54) INSPECTING SWATH BOUNDARIES PRODUCED BY THERMAL TRANSFER OF ORGANIC MATERIALS IN FORMING OLED DEVICES

(75) Inventors: Andrea S. Rivers, Bloomfield, NY (US); Michael L. Boroson, Rochester, NY (US)

(73) Assignee: Eastman Kodak Company, Rochester, NY (US)

( * ) Notice: Subject to any disclaimer, the term of this patent is extended or adjusted under 35 U.S.C. 154(b) by 307 days.

(21) Appl. No.: 10/654,784

(22) Filed: Sep. 4, 2003

(65) Prior Publication Data

US 2005/0052199 A1    Mar. 10, 2005

(51) Int. Cl.
*H01L 31/26* (2006.01)
*B41J 2/435* (2006.01)

(52) U.S. Cl. .......................... 438/14; 347/234

(58) Field of Classification Search ............ 438/14

See application file for complete search history.

(56) References Cited

U.S. PATENT DOCUMENTS

| 5,994,836 A | 11/1999 | den Boer et al. |
| 6,582,875 B1 | 6/2003 | Kay et al. |
| 6,844,891 B1 * | 1/2005 | Kay et al. .................. 347/234 |
| 2002/0149315 A1 | 10/2002 | Blanchet-Fincher |
| 2003/0068525 A1 | 4/2003 | Bellmann et al. |
| 2003/0148021 A1 | 8/2003 | Ishizuka |

FOREIGN PATENT DOCUMENTS

| EP | 1 028 001 | 8/2000 |
| WO | WO 2005/022661 | 3/2005 |

* cited by examiner

*Primary Examiner*—W. David Coleman
(74) *Attorney, Agent, or Firm*—Raymond L. Owens

(57) ABSTRACT

A method of inspecting an OLED device to locate and characterize defects in the registration of organic material(s) transferred from a donor in swaths in response to heat produced by a multichannel laser print head includes optically inspecting the OLED device after or during manufacture to identify the boundaries between swaths of transferred organic material(s), and determining if the swaths overlap at a seam of the boundary or if there is a gap between swath edges at the seam or if there is an offset between the edges of adjacent swaths.

7 Claims, 6 Drawing Sheets

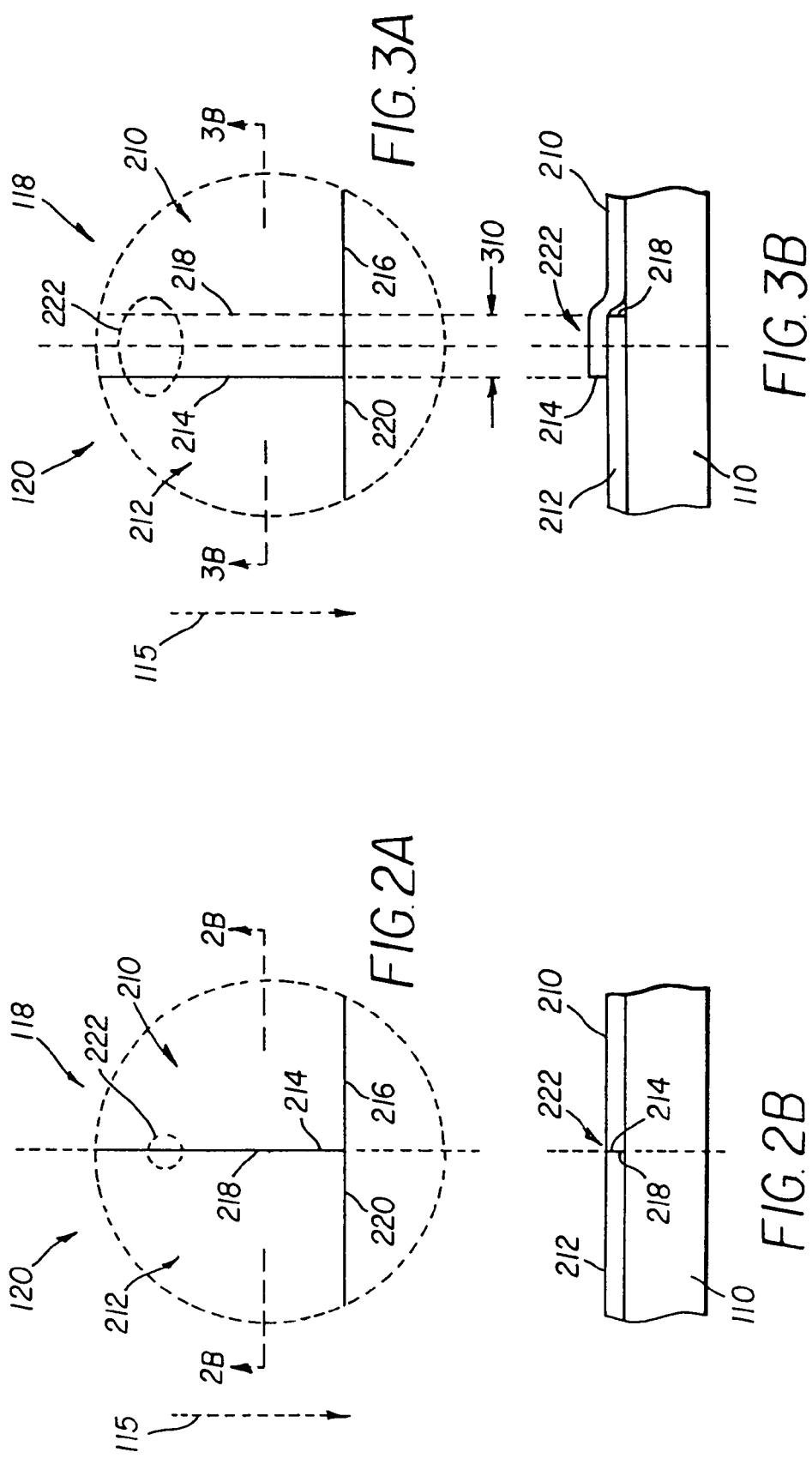

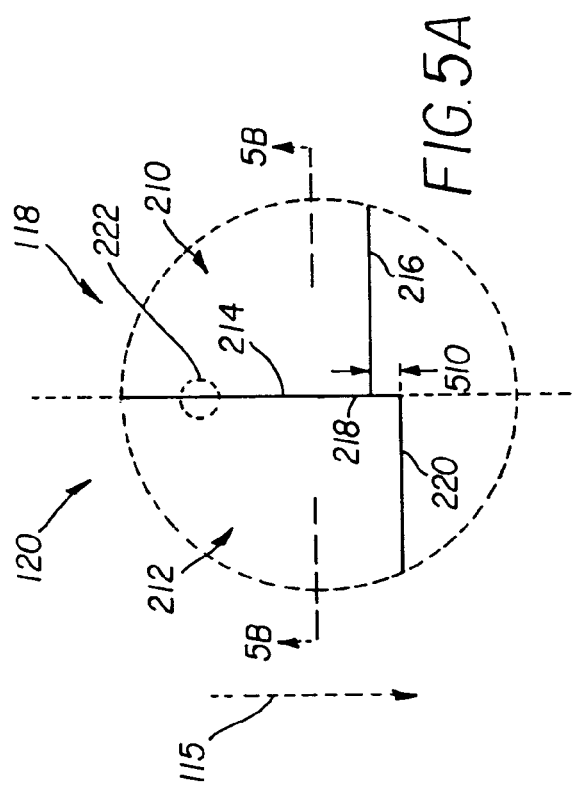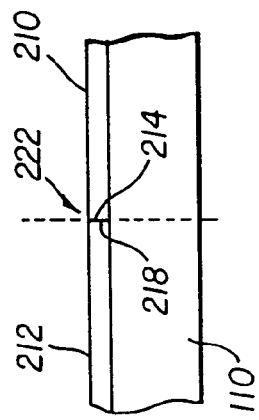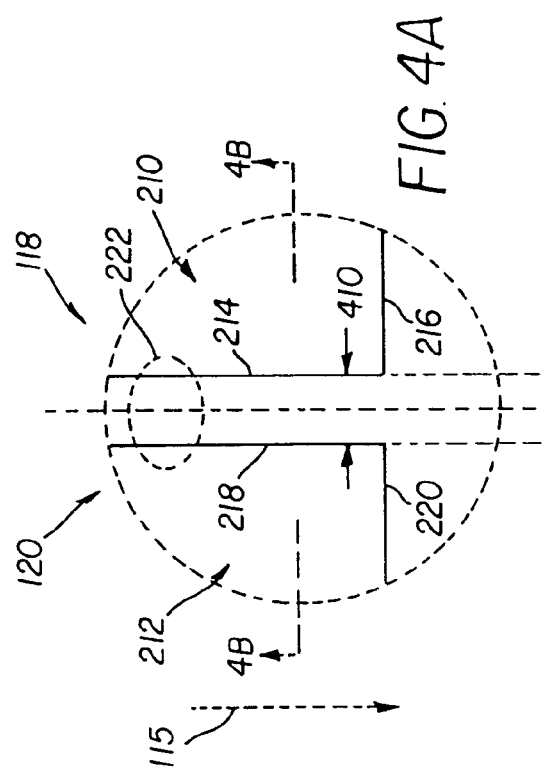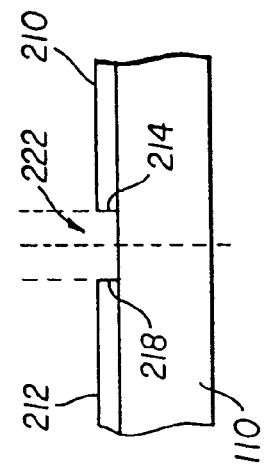

INSPECTING SWATH BOUNDARIES PRODUCED BY THERMAL TRANSFER OF ORGANIC MATERIALS IN FORMING OLED DEVICES

CROSS REFERENCE TO RELATED APPLICATION

Reference is made to commonly assigned U.S. patent application Ser. No. 10/184,417 filed Jun. 27, 2002 by Andrea S. Rivers et al., entitled "Depositing an Emissive Layer for Use in an Organic Light-Emitting Display Device (OLED)", now U.S. Pat. No. 6,682,863.

FIELD OF THE INVENTION

The present invention relates to organic light-emitting display devices, in particular, to methods of manufacturing and inspecting organic light-emitting diodes (OLEDS) formed by thermal transfer.

BACKGROUND OF THE INVENTION

OLEDs are useful in a variety of applications as discrete light-emitting devices, or as the active element of light-emitting arrays or displays, such as flat-panel displays in watches, telephones, laptop computers, pagers, cellular phones, calculators, and the like.

Conventional OLED display structures are built on glass substrates in a manner such that a two-dimensional OLED array for image manifestation is formed. Each OLED in the array generally includes overlying layers, starting with a light-transmissive first electrode formed on the substrate, an organic electroluminescent (EL) emission medium deposited over the first electrode, and a metallic electrode on top of the organic electroluminescent medium. When an electrical potential is placed across the electrodes, holes and electrons are injected into the organic zones from the anode and cathode, respectively. Light emission results from hole-electron recombination within the device.

Two primary technical challenges relating to OLED technology are materials and fabrication. Materials science, whether related to small molecules or polymers, holds the key to the industry's ability to improve lifetime and emission efficiency. Furthermore, given that the organic materials cannot come in contact with water or oxygen, fabrication is especially difficult. Well known shadow masked based vacuum deposition technology, using conventional vacuum chambers, is often used for manufacturing OLEDs. However, shadow mask based vacuum deposition technology is limited in the precision of the deposition geometry.

A laser thermal transfer (LTT) process is an example of an emerging technology for manufacturing OLEDs with potential advantages over conventional deposition processes. LTT is a process that uses heat to transfer an organic donor material (emitter material that is being transferred) onto a substrate. The donor material and substrate are held in a predetermined spatial relationship with respect to one another. The donor material includes a support layer, a thermal absorber layer and a layer of electroluminescent organic material. The LTT process includes using a laser beam that generates heat by impinging upon the absorber layer of the donor material, thereby creating heat, which vaporizes the organic material, which is subsequently deposited upon the target substrate in a predefined pattern. For example, U.S. Pat. No. 6,582,875 describes the process of using a multichannel laser print head, which transfers organic material to a patterned substrate. Several technical challenges exist for manufacturing OLEDs using the LTT process, such as implementing process monitoring and control techniques for ensuring a high-quality OLED structure. For example, visual artifacts can result if the print head is not properly aligned with the patterned substrate, or if the motion of the print head is not properly coordinated relative to the patterned substrate.

For example, U.S. Pat. No. 5,994,836 describes an organic light-emitting diode (OLED) array structure, and corresponding method of making the structure. Each OLED pixel includes a first electrode on a substrate, a second electrode on a substrate, and an organic emission layer disposed between the first and second electrodes so as to emit visible light when a suitable potential is applied thereto by the electrodes. In accordance with certain embodiments of this invention, a step covering or coverage layer is provided over step or edge areas of the first electrode in order to reduce the structure's susceptibility to breakdown at pixel edges, thereby improving yields. While U.S. Pat. No. 5,994,836 describes a suitable method of manufacturing an OLED structure, it provides no mention of process monitoring, in particular, process monitoring of an LTT process for manufacturing OLEDs.

SUMMARY OF THE INVENTION

It is therefore an object of the invention to provide a way to provide for the reduction of visual artifacts in OLED devices produced by a thermal transfer process.

This object is achieved by a method of inspecting an OLED device to locate and characterize defects in the registration of organic material(s) transferred from a donor in swaths in response to heat produced by a multichannel laser print head, comprising:

a) optically inspecting the OLED device after or during manufacture to identify the boundaries between swaths of transferred organic material(s); and b) determining if the swaths overlap at a seam of the boundary or if there is a gap between swath edges at the seam or if there is an offset between the edges of adjacent swaths.

A feature of the invention is that the present invention can be used to correct the manufacturing process to minimize visual artifacts. This can be accomplished either online or after manufacture. The swath boundary errors can be effectively used to correct the manufacturing process, providing continuous process monitoring and real time process control. In addition, the swath boundary errors can be used to guide the initial system setup. The methods of analyzing the physical characteristics of an OLED display device in accordance with the invention provide a way of ensuring and maintaining a high-quality fabrication process for OLED displays.

It is an advantage of the present invention to use the swath boundaries produced in the thermal transfer of organic material(s) to determine if there are or will be visual artifacts in the OLED device.

BRIEF DESCRIPTION OF THE DRAWINGS

FIG. 2A illustrates an expanded view of detail A of FIG. 1 showing an ideal swath-to-swath seam;

FIG. 2B illustrates a cross-sectional view taken along the lines 2—2 of FIG. 2A;

FIG. 3A illustrates an expanded view of detail A of FIG. 1 showing a first example of a misaligned swath-to-swath seam;

FIG. 3B illustrates a cross-sectional view taken along lines 3—3 of FIG. 3A;

FIG. 4A illustrates an expanded view of detail A of FIG. 1 showing a second example of a misaligned swath-to-swath seam;

FIG. 4B illustrates a cross-sectional view taken along the lines 4—4 of FIG. 4A;

FIG. 5A illustrates an expanded view of detail A of FIG. 1 showing a third example of a misaligned swath-to-swath seam;

FIG. 5B illustrates a cross-sectional view taken along the lines 5—5 of FIG. 5A;

DETAILED DESCRIPTION OF THE INVENTION

The present invention is a method of utilizing the inherent and unique swath-to-swath physical characteristics of an OLED display device formed with an LTT process 100, whereby these unique swath-to-swath physical characteristics are optically observed and analyzed for the purpose of verifying initial system setup, real-time process control, and continuous process monitoring. The methods of analyzing the physical characteristics of an OLED display device in accordance with the invention provide a way of ensuring and maintaining a high-quality fabrication process for OLED displays.

For a better understanding of the invention, FIGS. 1, 2A, 2B, 3A, 3B, 4A, 4B, 5A, and 5B below are provided for background, while subsequent FIGS. 6, 7, and 8 relate to the specific embodiments of the invention.

Figure 1:
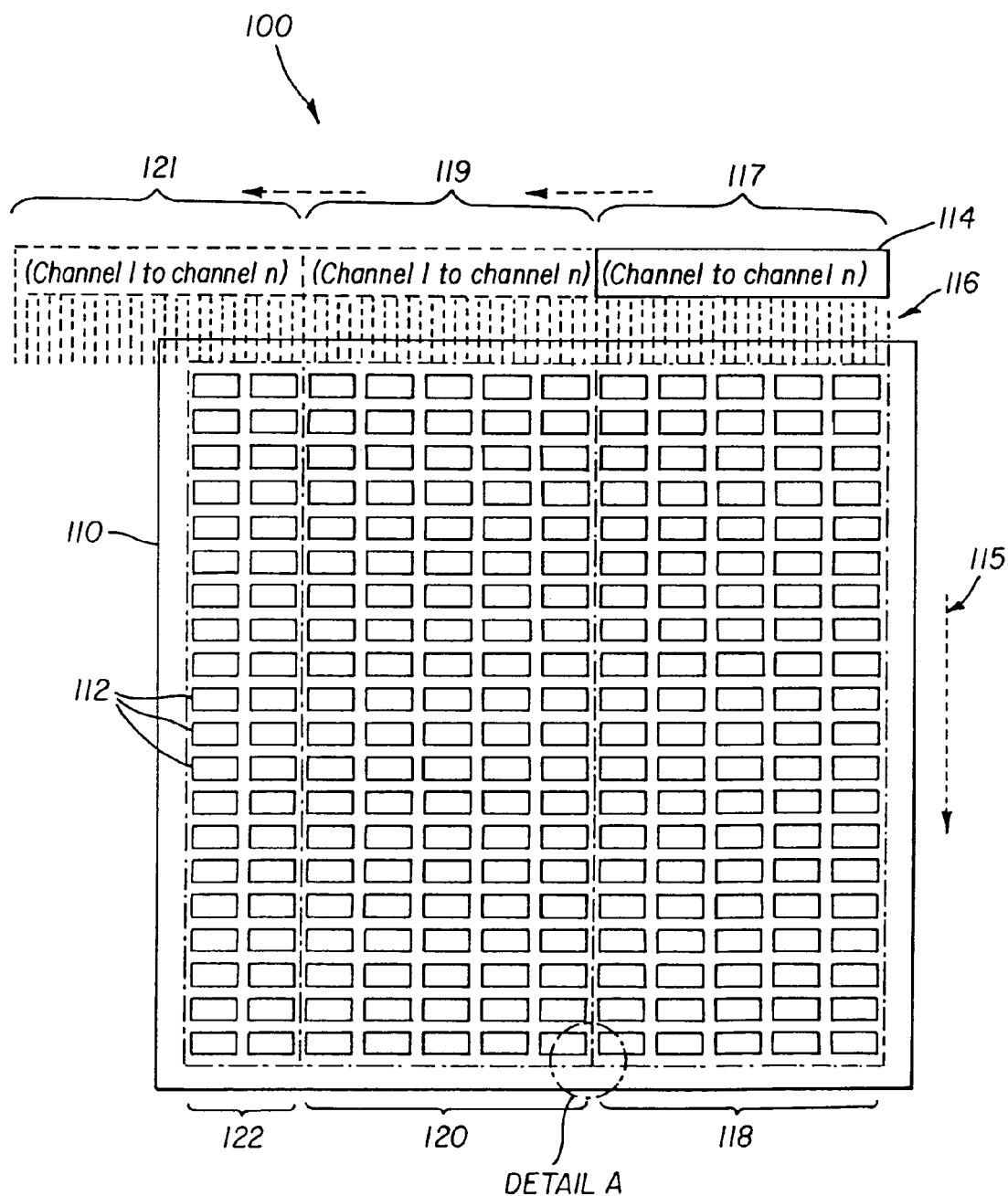
FIG. 1 illustrates features of a laser thermal transfer, LTT, method or process showing the relationship between the multichannel print head portion of an LTT station and the substrate during the process of fabricating OLED displays.

FIG. 1 illustrates an example of a laser thermal transfer process, or LTT process 100, during the process of fabricating OLED displays. LTT process 100 includes a conventional substrate 110 formed of, for example, glass, upon which an array layout of a plurality of pixel locations 112 is shown. LTT process 100 further includes a multichannel laser thermal print head 114 wherein a plurality of channels 1 through n of multichannel laser thermal print head 114 are each representative of a laser beams 116; thus, a plurality of laser beams 116 are Generated. However, a summary of the operation of LTT process 100 as shown in FIG. 1 is provided below.

Multichannel laser thermal print head 114 is a conventional laser thermal print head that receives a single laser beam input (not shown) that is subsequently split into multichannels, for example, 256 channels, for generating output laser beams 116. Multichannel laser thermal print head 114 permits for individual control of each channel, thereby providing on/off control of each individual laser beam 116. The multichannel laser thermal print head 114 can, for example, be a Gen III KPG LT print head manufactured by Kodak Polychrome Graphics (Norwalk, Conn.) having 256 channels, a power range of between 16 and 24 watts, and an output wavelength of ~808 nm. Multichannel laser thermal print head 114 is mounted upon a motion control system (not shown) that provides multichannel laser thermal print head 114 with precision X, Y, and theta (Θ) motion relative to substrate 110. A donor (not shown) formed of a transparent substrate atop which is deposited an organic transfer layer, typically formed of electroluminescent organic material, is physically arranged between multichannel laser thermal print head 114 and substrate 110.

Although those skilled in the art will appreciate that a mix of pixel colors are possible, for simplicity, the operation of LTT process 100 is described with the assumption that all pixel locations 112 are of one color, for example, pixel locations 112 are all red, all green, or all blue. In operation, the input laser source that feeds multichannel laser thermal print head 114 is activated, thereby generating selected laser beams 116 based upon the predefined pattern array of pixel locations 112, such as shown in FIG. 1. Laser beams 116 impinge upon the donor in this predefined pattern as multichannel laser thermal print head 114 sweeps across substrate 110 in a fast scan direction 115 as shown in FIG. 1. The conversion of the energy of laser beams 116 to heat sublimates the organic material of the donor, thereby vaporizing the organic material and depositing the organic material in the desired pattern upon substrate 110.

Since, in this example, the width of substrate 110 is greater than the width of multichannel laser thermal print head 114, multichannel laser thermal print head 114 must make multiple passes to expose the entire area of substrate 110. With continuing reference to FIG. 1, multichannel laser thermal print head 114 is initially positioned toward one edge of substrate 110 at step 117 and sweeps in the fast scan direction 115 along substrate 110, thereby depositing a first swath 118 of organic material. Subsequently, multichannel laser thermal print head 114 is stepped the full width of multichannel laser thermal print head 114 in a direction perpendicular to the fast scan direction 115 to step 119 and again sweeps in the fast scan direction 115 along substrate 110, thereby depositing a second swath 120 of organic material, which abuts an edge of swath 118. Lastly, multichannel laser thermal print head 114 is stepped again the full width of multichannel laser thermal print head 114 in a direction perpendicular to the fast scan direction 115 to step 121 and again sweeps in the fast scan direction 115 along substrate 110, thereby depositing a third swath 122 of organic material, which abuts an edge of swath 120. In all cases, the appropriate channels, i.e., laser beams 116, are activated in a manner that correlates to the width of swath 118, swath 120, or swath 122, and to the desired pattern of pixel locations 112.

In this example, the boundaries of swath 118, swath 120, and swath 122 fall in the non-pixel region (i.e., between columns of pixel locations 112). However, it is noted that these swath boundaries, or "seams", can fall anywhere across the width of substrate 110, even within the pixel regions. FIGS. 2A, 2B, 3A, 3B, 4A, 4B, 5A, and 5B below show an expanded view of a detail A of FIG. 1 and illustrate possible characteristics of a swath-to-swath boundary that are an indication of the process quality. These swath-to-swath boundary characteristics can be monitored via visual inspection using standard optical equipment. Such inspection equipment can include an Olympus Provis Research microscope equipped with fluorescent light at wavelengths of 365 and 470 nm and an instrumented stage with controlling hardware and software as well as image processing software. Both the instrumented stage and image processing software can be provided by Media Cybernetix, for example Image Pro software and Stage Pro software. It should be noted that this embodiment describes an optical inspection process. Other detection techniques such as, but not limited to capacitive measurements or spectroscopic ellipsometry could be used, as well.

FIG. 2A illustrates an expanded view of detail A of FIG. 1 showing an ideal swath-to-swath seam 222 between swath 118 and swath 120. More specifically, this expanded view shows that swath 118 is formed of an organic layer 210 and that swath 120 is formed of an organic layer 212. Organic layer 210 is bounded by an edge 214 along the fast scan direction and an edge 216 perpendicular to the fast scan direction 115. Similarly, organic layer 212 is bounded by an edge 218 along the fast scan direction 115 and an edge 220 perpendicular to the fast scan direction 115. The boundary between edge 214 of organic layer 210 and edge 218 of organic layer 212 forms seam 222.

FIG. 2B illustrates a cross-sectional view taken along the lines 2—2 of FIG. 2A. With reference to FIGS. 2A and 2B, it is shown that there is no overlap of or gap between edge 214 of organic layer 210 and edge 218 of organic layer 212, thereby forming a seam 222 where edge 214 of organic layer 210 and edge 218 of organic layer 212 perfectly abut. Furthermore, edge 216 of organic layer 210 and edge 220 of organic layer 212 are likewise perfectly aligned at seam 222 along a line perpendicular to the fast scan direction. A device with such swath boundaries would exhibit minimal swath boundary image artifacts.

FIG. 3A illustrates an expanded view of detail A of FIG. 1 showing a first example of a misaligned swath-to-swath seam 222 between swath 118 and swath 120. FIG. 3B illustrates a cross-sectional view taken along the lines 3—3 of FIG. 3A. With reference to FIGS. 3A and 3B, it is shown that there is an overlap 310 formed by edge 214 of organic layer 210 overlapping edge 218 of organic layer 212, thereby forming a seam 222 where edge 214 of organic layer 210 and edge 218 of organic layer 212 do not perfectly abut. However, edge 216 of organic layer 210 and edge 220 of organic layer 212 are perfectly aligned at seam 222 along a line perpendicular to the fast scan direction. A device with such swath boundaries would exhibit swath boundary image artifacts such as dark stripes if said boundaries occur within a pixel location 112.

FIG. 4A illustrates an expanded view of detail A of FIG. 1 showing a second example of a misaligned swath-to-swath seam 222 between swath 118 and swath 120. FIG. 4B illustrates a cross-sectional view taken along the lines 4—4 of FIG. 4A. With reference to FIGS. 4A and 4B, it is shown that there is a gap 410 formed between edge 214 of organic layer 210 and edge 218 of organic layer 212, thereby forming a seam 222 where edge 214 of organic layer 210 and edge 218 of organic layer 212 do not perfectly abut. However, edge 216 of organic layer 210 and edge 220 of organic layer 212 are perfectly aligned at seam 222 along a line perpendicular to the fast scan direction 115. A device with such swath boundaries would exhibit swath boundary image artifacts such as bright stripes if said boundaries occur within a pixel location 112.

FIG. 5A illustrates an expanded view of detail A of FIG. 1 showing a third example of a misaligned swath-to-swath seam 222 between swath 118 and swath 120. FIG. 5B illustrates a cross-sectional view taken along the lines 5—5 of FIG. 5A. With reference to FIGS. 5A and 5B, it is shown that there is no overlap of or gap between edge 214 of organic layer 210 and edge 218 of organic layer 212, thereby forming a seam 222 where edge 214 of organic layer 210 and edge 218 of organic layer 212 perfectly abut. However, edge 216 of organic layer 210 and edge 220 of organic layer 212 are not perfectly aligned at seam 222 along a line perpendicular to the fast scan direction, thereby forming an offset 510. A device with such swath boundaries would exhibit swath boundary image artifacts if said boundaries occur within a pixel location 112. The resulting image artifacts would involve incomplete coverage with organic material of various pixel locations 112.

The swath-to-swath characteristics as described above in FIGS. 2A, 2B, 3A, 3B, 4A, 4B, 5A, and 5B are illustrative in nature; any combination of overlap 310, gap 410, or offset 510 is possible together with other structural characteristics along seam 222. For example, in the case in which seam 222 (ideal or otherwise) falls within pixel location 112, a discontinuity in the light emission of the affected pixel is observable. All such characteristics/defects are observable and measurable with standard optical instrumentation and are an indicator of process quality. Furthermore, these inherent structural swath-to-swath characteristics, such as those described in FIGS. 2A, 2B, 3A, 3B, 4A, 4B, 5A, and 5B, are unique to an LTT process 100 using a multichannel laser thermal print head 114, such as LTT process 100. Thus, the manufacturing process of an OLED display can be determined by simple visual observation. For example, an OLED display manufactured using a shadow mask deposition process does not possess these same structural characteristics, particularly those characteristics associated with swaths.

Alternately, the swath-to-swath characteristics as described above in FIGS. 2A, 2B, 3A, 3B, 4A, 4B, 5A, and 5B are illustrative in nature; any combination of overlap 310, gap 410, or offset 510 is possible together with other structural characteristics along seam 222. For example, in the case in which seam 222 (ideal or otherwise) falls outside of a pixel location 112, the emissions in response to the appropriate wavelength of light enable the observation of the seam. Such observations would require examination of the substrate following the deposition step and prior to further processing of the device. All such characteristics/defects are observable and measurable with standard optical instrumentation and are an indicator of process quality. Furthermore, these inherent structural swath-to-swath characteristics, such as those described in FIGS. 2A, 2B, 3A, 3B, 4A, 4B, 5A, and 5B, are unique to an LTT process 100 using a multichannel laser thermal print head 114, such as LTT process 100. Thus, the manufacturing process of an OLED display is determined by a simple visual observation. For example, an OLED display manufactured using a shadow mask deposition process does not possess these same structural characteristics, particularly those characteristics associated with swaths.

Figure 6:
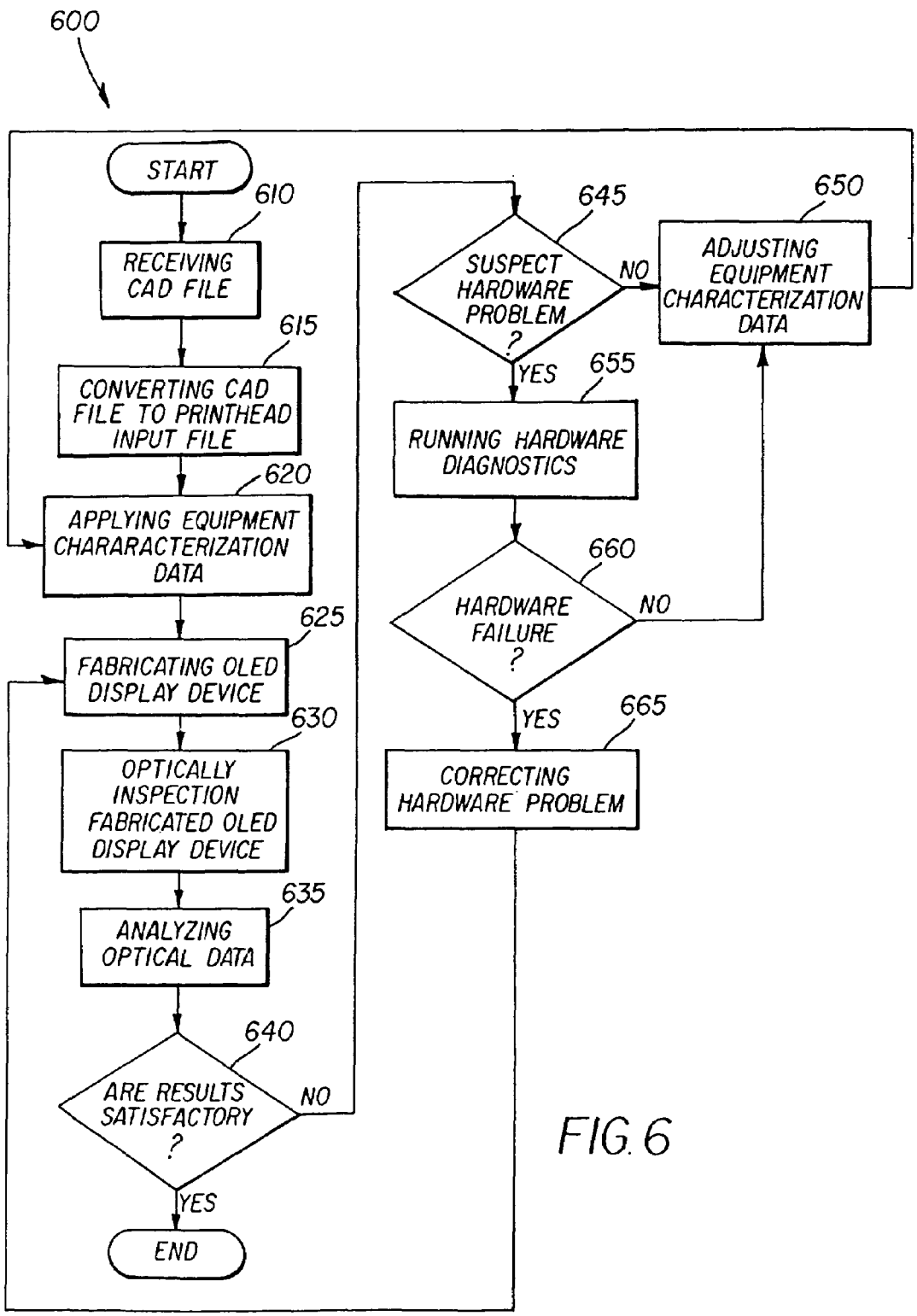
FIG. 6 shows a flow diagram of a method of an initial OLED display fabrication using an LTT process in accordance with the invention.

FIG. 6 shows a flow diagram of a method 600 of initial OLED display fabrication using an LTT process in accordance with the invention. Method 600 is suitable for use in the initial system setup for verifying the functionality of a raster image processor (RIP), for verifying proper control software implementation (proper CAD file-to-print head control conversion), for verifying positioning accuracy of the equipment, and for verifying proper equipment operation. Method 600 includes the following steps:

In step 610, a CAD file associated with a given OLED display device is received from a designer and processed with conventional methods such as parsing and design rule checking. Optionally, the CAD file can include data for forming a test pattern upon the OLED display device. Method 600 proceeds to step 615.

In step 615, the CAD file is converted to a file format suitable for input to an LTT print head, such as multichannel laser thermal print head 114 of LTT process 100 (FIG. 1). More specifically, a CAD file representing a given OLED display is converted via the RIP to an image file that provides input to LTT process 100. For example, the process for converting the CAD file to a print head input file can include converting to a binary map, followed by creating an image file, followed by generating a corrected binary map and a machine instruction file, which is subsequently fed into LTT process 100. Method 600 proceeds to step 620.

In step 620, if available, equipment characterization data is applied to LTT process 100. In this case, the corrected binary map and machine instruction file are modified to reflect the characteristics of the manufacturing equipment. Method 600 proceeds to step 625.

In step 625, the OLED display device is fabricated using an LTT process such as LTT process 100 according to the specifications of the CAD file received in step 610. This OLED display device can optionally include a test pattern printed thereon. Method 600 proceeds to step 630.

In step 630, the finished OLED display device is optically inspected using conventional optical instrumentation, such as an Olympus Provis Research microscope equipped with fluorescent light at wavelengths of 365 and 470 nm and an instrumented stage with controlling hardware and software as well as image processing software. Both the instrumented stage and image processing software can be provided by Media Cybernetix, for example Image Pro software and Stage Pro software. Optical data is converted via image processing software and custom software into data, which characterizes the fabricated OLED display device. This data is used by, for example, a controller associated with LTT process 100. The optical data includes information, for example, relating to the physical characteristics of the swath-to-swath boundary (seam 222), variations of which are described in reference to FIGS. 2A, 2B, 3A, 3B, 4A, 4B, 5A, and 5B. Method 600 proceeds to step 635.

In step 635, a user or software application analyzes the optical data generated in step 630 for all phases of the fabrication process of the OLED display device. Examples of data analysis include analysis of any misregistration between the transfer area relative to the target area, i.e., verifying the corner locations of the transfer area relative to the corner locations of a sampling of pixel locations 112; and analysis of the swath boundaries, i.e., identifying and verifying the locations and physical characteristics of swath overlap, gap or offset. Method 600 proceeds to step 640.

In decision step 640, based upon the optical data analysis of step 635, a user or software application determines whether the quality of the physical characteristics of the fabricated OLED display device is satisfactory. For example, are the swath overlap, gap or offset are sufficient to require correction. If no correction is deemed appropriate, method 600 ends. If correction is required, method 600 proceeds to step 645.

In decision step 645, it is determined whether the poor results as indicated via the optical data analysis are due to a suspected hardware problem. The following are three examples, for illustration. In one case, a multichannel laser thermal print head 114 failure can be noted. Here, a lack of coverage can be detected in all swaths and can be associated with a failure of specific channels within the multichannel laser thermal print head 114. In another case, a distortion can be gradually introduced during the creation of a display device. Should the vacuum chamber fail to maintain the vacuum level within the acceptable limits during the LTT process 100 for a substrate 110, misregistration between the transfer area relative to the target area will change from swath to swath in accordance with the changes to the vacuum loading of the window through which the multichannel laser thermal print head 114 light passes. And finally, the third case involves a failure of the motion control system feedback system. Since this feedback system is utilized to drive the transfer of data to the multichannel laser thermal print head 114, a disruption of this signal will cause a related disruption of organic deposition. For example, should the position feedback device have been damaged, or become misaligned, a region within the travel of the print head can experience a short distance during which the feedback signals dropout. Should this occur, the length in the fast scan direction shall be extended by a distance proportional to the number of dropouts and subsequent misregistration between the transfer area relative to the target area will demonstrate a consistent shift of the same magnitude. If yes, method 600 proceeds to step 655. If no, method 600 proceeds to step 650.

In step 650, adjustments are made to the equipment characterization data to accommodate the changing performance of the laser thermal transfer process. The resulting changes are then processed via the RIP and an adjusted image file is provided as input to LTT process 100. Method 600 returns to step 620.

In step 655, hardware diagnostics are performed on the equipment included in the LTT manufacturing process. Examples of potentially failed equipment include a system controller; an X, Y, and Θ motion control system; a vacuum chamber and associated controls; a laser source and associated optical devices; and a print head, such as multichannel laser thermal print head 114. Method 600 proceeds to step 660.

In step 660, a user or software application interprets the results of the hardware diagnostics to determine whether a hardware failure is present. If yes, method 600 proceeds to step 665. If no, method 600 proceeds to step 650.

In step 665, a user or technician makes the appropriate hardware repair, thus eliminating the hardware failure and restoring the operable condition of LTT process 100. Method 600 returns to step 625.

Figure 7:
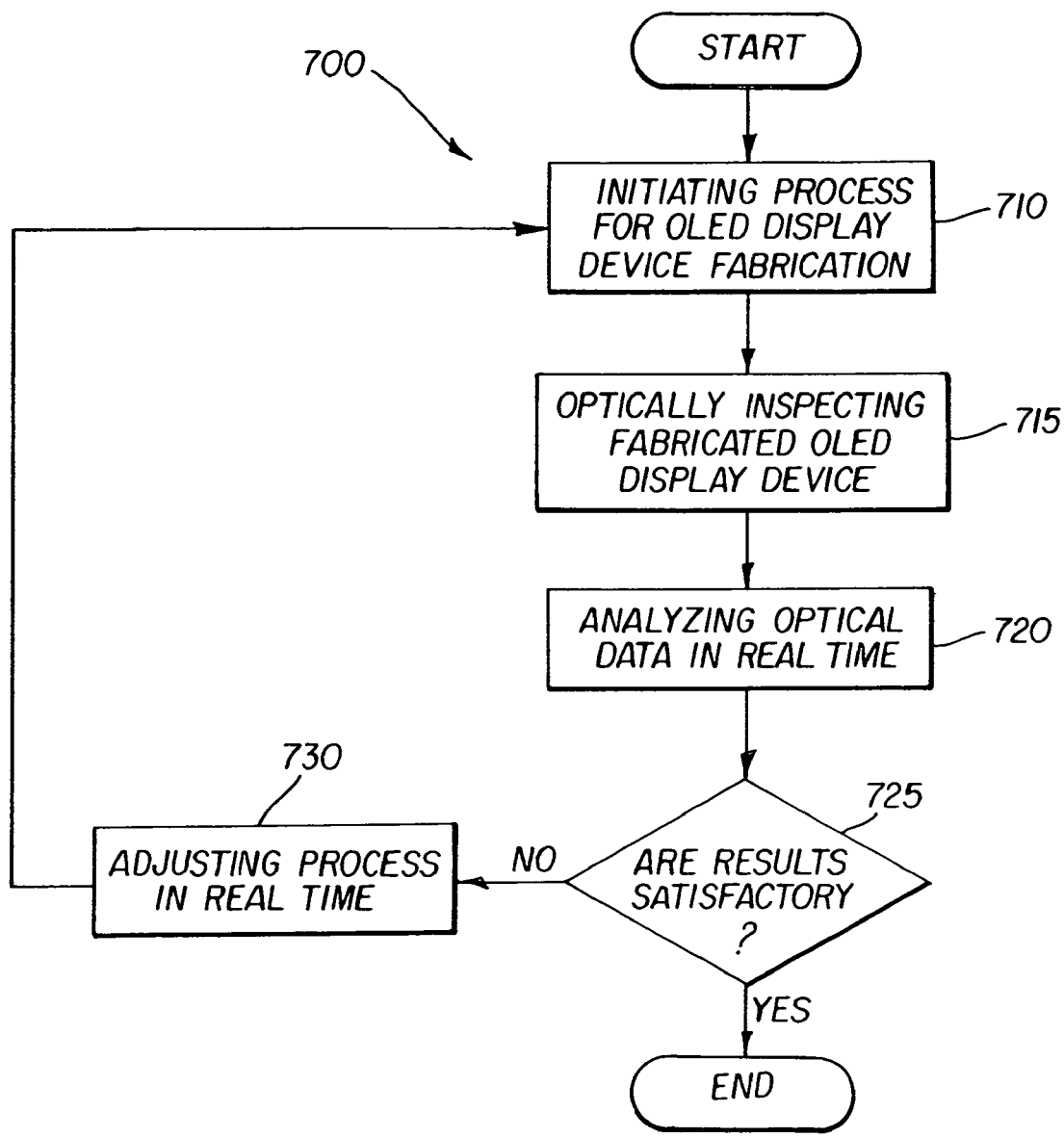
FIG. 7 shows a flow diagram of a method of real-time process control for the fabrication of OLED display devices using an LTT process in accordance with the invention.

FIG. 7 shows a flow diagram of a method 700 of real-time process control for the fabrication of OLED display devices using an LTT process in accordance with the invention. Method 700 includes the following steps:

In step 710, an LTT process, such as LTT process 100, is initiated for the continuous manufacturing of OLED display devices that are fabricated according to predetermined design specifications. More specifically, specifications are generated via a CAD file representing a given OLED display. The CAD file is then is converted via a RIP into an image file that provides input in the form of instructions that can be interpreted by LTT process 100. Method 700 proceeds to step 715.

In step 715, periodically during the manufacturing process a sample OLED display device is optically inspected using conventional optical instrumentation, such as listed above. Such inspection equipment can include an Olympus Provis Research microscope equipped with fluorescent light at wavelengths of 365 and 470 nm with controlling hardware and software as well as image processing software. The image processing software can be provided by Media Cybernetix, for example Image Pro software and Stage Pro software. Optical data associated with the characterization of this sample OLED display device is generated and stored in, for example, a controller associated with LTT process 100. The optical data includes information relating to, for example, the physical characteristics of the swath-to-swath boundary (seam 222), variations of which are described in reference to FIGS. 2A, 2B, 3A, 3B, 4A, 4B, 5A, and 5B. Method 700 proceeds to step 720.

In step 720, a user or software application performs real-time analysis of the optical data generated in step 715 for all phases of the fabrication process of the OLED display device. Examples of data analysis include analysis of the location of a test pattern in relation to a fiducial; analysis of any misregistration between the transfer area relative to the target area, i.e., verifying the corner locations of the transfer area relative to the corner locations of a sampling of pixel locations 112; and analysis of the swath boundaries, i.e., identifying and verifying the locations and physical characteristics of swath overlap, gap or offset. Method 700 proceeds to step 725.

In step 725, based upon the optical data analysis of step 720, a user or software application determines whether the quality of the physical characteristics of the fabricated OLED display device is satisfactory. For example, are the swath overlap, gap or offset are sufficient to require correction. If no correction is deemed appropriate, method 700 ends. If correction is required, method 700 proceeds to step 730.

In step 730, real-time adjustments are made to LTT process 100 as warranted by the results of the optical data analysis. Examples of real-time process adjustments include, but are not limited to, adjusting the angle of the print head (i.e., multichannel laser thermal print head 114), making adjustments for mechanical thermal variations, recalibrating position sensors, recalibrating the print head and generating a new corrected binary map and metadata file. Method 700 then returns to step 710.

Figure 8:
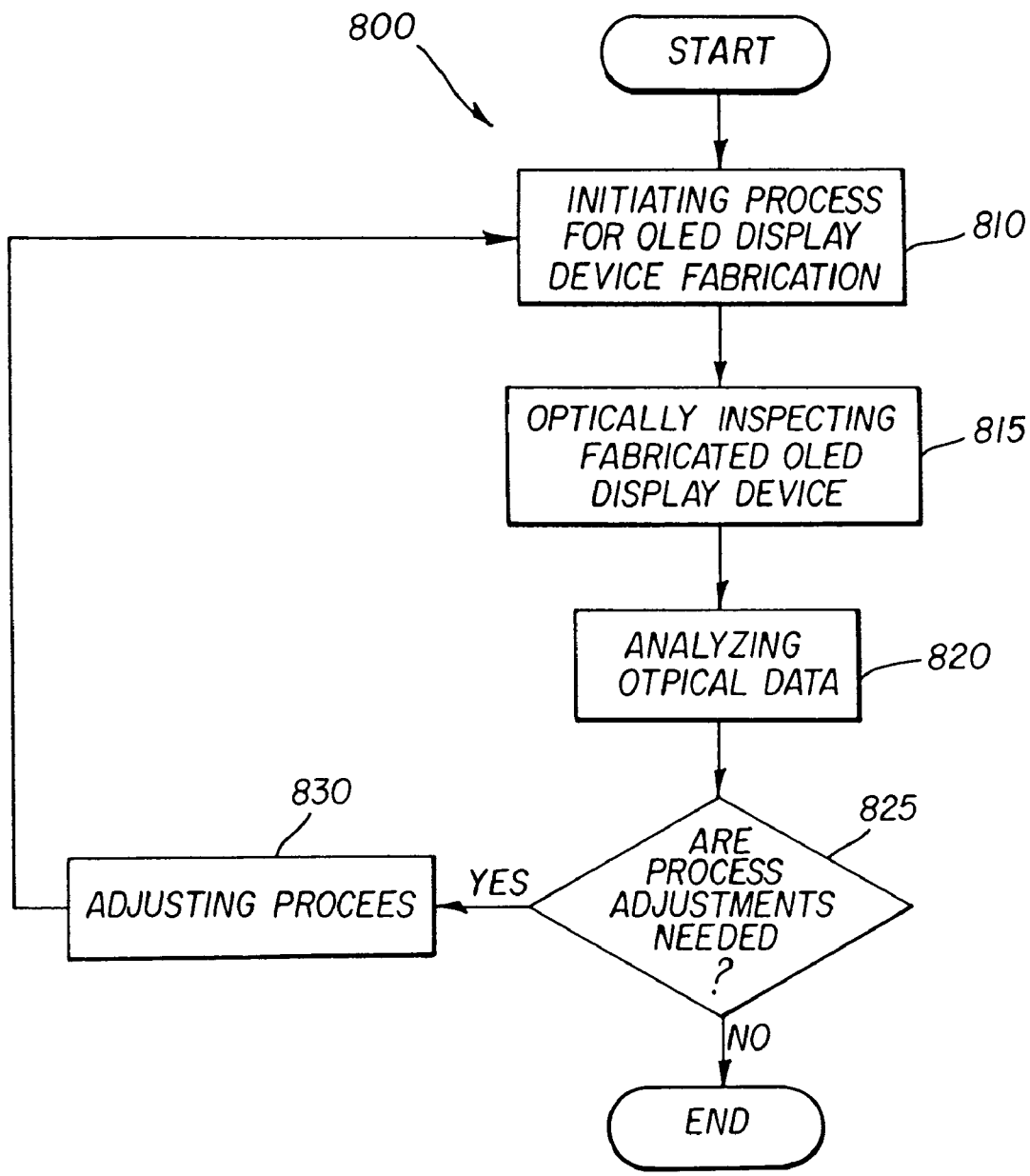
FIG. 8 shows a flow diagram of a method of continuous process monitoring and control for the fabrication of OLED display devices using an LTT process in accordance with the invention.

FIG. 8 shows a flow diagram of a method 800 of continuous process monitoring and control for the fabrication of OLED display devices using an LTT process in accordance with the invention. Method 800 can be differentiated from method 700 in that method 700 provides for correcting the manufacturing process during production of the OLED device, while method 800 provides for correcting the manufacturing process after production of the OLED device. In both cases correcting the manufacturing process is prompted by the determination that the overlap, gap or offset were sufficient to require manufacturing process correction. Method 800 includes the following steps:

In step 810, an LTT process, such as LTT process 100, is initiated for the continuous manufacturing of OLED display devices that are fabricated according to predetermined design specifications. More specifically, specifications are generated via a CAD file representing a given OLED display. The CAD file is then is converted via a RIP into an image file that provides input in the form of instructions that can be interpreted by LTT process 100. Method 800 proceeds to step 815.

In step 815, periodically throughout the manufacturing process a sample OLED display device is selected and optically inspected using conventional optical instrumentation. Such equipment can include, for example, a high-resolution Sony CCD camera equipped with fluorescent light at wavelengths of 365 and 470 nm and image processing software provided by Media Cybemetix, for example Image Pro software or IMAQ provided by National Instruments. Optical data associated with the characterization of this sample OLED display device is generated and stored in, for example, a controller associated with LTT process 100. The optical data includes information relating to, for example, the physical characteristics of the swath-to-swath boundary (seam 222), variations of which are described in reference to FIGS. 2A, 2B, 3A, 3B, 4A, 4B, 5A, and 5B. Method 800 proceeds to step 820.

In step 820, a user or software application analyzes the optical data generated in step 815 for all phases of the fabrication process of the OLED display device. Examples of data analysis include analysis of the location of a test pattern in relation to a fiducial; analysis of any misregistration between the transfer area relative to the target area, i.e., verifying the corner locations of the transfer area relative to the corner locations of a sampling of pixel locations 112; and analysis of the swath boundaries, i.e., identifying and verifying the locations and physical characteristics of swath overlap, gap or offset. Method 800 proceeds to step 825.

In step 825, based upon the optical data analysis of step 820 over time, a user or software application identifies trends within the fabrication process that adversely affect the quality of the fabricated OLED display devices and thus warrant adjustments within the fabrication process. For example, trends in swath overlap, gap or offset can be identified. Other trends can be identified that indicate a gradual deterioration of some phase of the fabrication process, such as a gradual deterioration of the laser source, the print head, or the alignment system or changes related to trends in system temperature or vacuum levels. Alternately a trend can be found to occur during the creation of a single substrate. If process adjustments are needed, method 800 proceeds to step 830. If not, method 800 ends.

In step 830, adjustments are made to LTT process 100 as warranted by the results of the optical data analysis. Examples of process adjustments include, but are not limited to, replacing or calibrating the print head (i.e., multichannel laser thermal print head 114), selecting another RIP file, adjusting the gap between substrate 110 and multichannel laser thermal print head 114, adjustment to machine control parameters such that parameters which impact trends occurring within the manufacture of one substrate can be modified such that an optimal distribution of visual artifacts is achieved, and calibrating the alignment system. Method 800 then returns to step 810.

Methods 600, 700, and 800 of the present invention can generally apply to any LTT printing deposition process used, for example, for thick film circuitry deposition, where a multichannel print head deposition process is used in lieu of other well known deposition processes, such as a shadow mask process.

The invention has been described in detail with particular reference to certain preferred embodiments thereof, but it will be understood that variations and modifications can be effected within the spirit and scope of the invention.

PART LIST

100 LTT process
110 substrate
112 pixel locations
114 multichannel laser thermal print head
115 fast scan direction
116 laser beams
117 step
118 swath
119 step
120 swath
121 step 122 swath
210 organic layer
212 organic layer
214 edge
216 edge
218 edge
220 edge
222 seam
310 overlap
410 gap
510 offset
600 method
610 block
615 block
620 block
625 block
630 block
635 block
640 block
645 block
650 block
655 block
660 block
665 block
670 method
710 block
715 block
720 block
725 block
730 block
800 method
810 block
815 block
820 block
825 block
830 block

What is claimed is:

1. A method of inspecting an OLED device to determine if organic material(s) transferred from a donor in swaths in response to heat produced by a multichannel laser print head have been produced to minimize visual artifacts produced by the OLED device, comprising:

a) optically inspecting the OLED device after or during a manufacturing process to identify the boundaries between swaths of transferred organic material(s);

b) determining if the swaths overlap at a seam of the boundary or determining if there is a gap between swath edges at the seam or if there is an offset between the edges of adjacent swaths; and c) determining if the overlap, gap or offset are sufficient to require correction in the manufacturing process.

2. The method of claim 1 further including correcting the manufacturing process either after the production of the OLED device or during OLED device production in response to the determination if the overlap, gap or offset were sufficient to require manufacturing process correction.

3. A method of manufacturing an OLED device comprising:

a) operating a multichannel laser print head in response to an image file to cause the transfer of organic material(s) thermally transferred from a donor in swaths to the OLED device, comprising:

b) optically inspecting the OLED device after or during a manufacturing process to identify the boundaries between swaths of transferred organic material(s);

c) determining if the swaths overlap at a seam of the boundary or determining if there is a gap between swath edges at the seam or if there is an offset between the edges of adjacent swaths; and d) correcting the image file if the overlap, gap or offset are sufficient to require correction in the manufacturing process.

4. The method of claim 3 further including producing the image file by using a CAD file and equipment characterization data.

5. The method of claim 4 wherein the act of correcting the image artifact includes changing the machine instruction file.

6. The method of claim 3 further including determining the distribution of visual artifacts across the OLED device.

7. The method of claim 6 further including using the distribution of visual artifacts to identify problems in manufacturing equipment.

* * * * *